(12) United States Patent
Searle et al.

(10) Patent No.: US 10,595,940 B2
(45) Date of Patent: Mar. 24, 2020

(54) LASER SYSTEMS AND RELATED METHODS

(71) Applicant: CooperSurgical, Inc., Trumbull, CT (US)

(72) Inventors: Denzil Searle, Cornwall (GB); David Charles Lansdowne, Falmouth (GB); Hans Forrer, St. Gallen (CH)

(73) Assignee: CooperSurgical, Inc., Trumbull, CT (US)

( * ) Notice: Subject to any disclaimer, the term of this patent is extended or adjusted under 35 U.S.C. 154(b) by 142 days.

(21) Appl. No.: 15/491,141

(22) Filed: Apr. 19, 2017

(65) Prior Publication Data
US 2017/0304001 A1    Oct. 26, 2017

Related U.S. Application Data

(60) Provisional application No. 62/325,085, filed on Apr. 20, 2016.

(51) Int. Cl.
*A61B 18/20* (2006.01)
*G02B 19/00* (2006.01)
(Continued)

(52) U.S. Cl.
CPC .............. *A61B 18/20* (2013.01); *A61B 17/43* (2013.01); *A61N 5/0601* (2013.01);
(Continued)

(58) Field of Classification Search
CPC ............ A61B 18/20; A61B 2018/2015; A61B 2018/2035; A61B 2018/20359;
(Continued)

(56) References Cited

U.S. PATENT DOCUMENTS 4,901,718 A * 2/1990 Bille ...................... A61B 18/20
606/18
5,051,558 A * 9/1991 Sukhman ........... B23K 26/0643
219/121.63
(Continued)

FOREIGN PATENT DOCUMENTS

DE      197 06 053      8/1998  ............... G02B 6/35
WO    WO 2004/069993   8/2004

OTHER PUBLICATIONS

International Search Report and Written Opinion of the International Searching Authority for International Application No. PCT/US2017/028398 by Examiner Matthias Beutter dated Aug. 4, 2017 (19 pages).

(Continued)

*Primary Examiner* — Ahmed M Farah
(74) *Attorney, Agent, or Firm* — Fish & Richardson P.C.

(57) ABSTRACT

A laser system includes a collimator configured to output a collimated laser beam, a support member to which the collimator is mounted, and a linear rail along which the support member is movable in a first dimension such that the collimator, mounted to the support member, and the collimated laser beam, outputted from the collimator, are movable in the first dimension. The laser system further includes a lens positioned downstream of the collimator and configured to direct the collimated laser beam to a target location on a specimen.

19 Claims, 8 Drawing Sheets

(51) Int. Cl.
*G02B 7/02* (2006.01)
*G02B 26/10* (2006.01)
*B23K 26/08* (2014.01)
*G02B 26/08* (2006.01)
*A61B 17/43* (2006.01)
*A61N 5/06* (2006.01)
*G02B 21/02* (2006.01)
*G02B 27/10* (2006.01)
*G02B 27/30* (2006.01)
*G02B 21/00* (2006.01)
*A61B 18/00* (2006.01)

(52) U.S. Cl.
CPC .......... *B23K 26/0869* (2013.01); *G02B 7/023* (2013.01); *G02B 19/009* (2013.01); *G02B 21/02* (2013.01); *G02B 26/0875* (2013.01); *G02B 26/103* (2013.01); *G02B 27/1006* (2013.01); *G02B 27/30* (2013.01); *A61B 2018/00559* (2013.01); *A61B 2018/00577* (2013.01); *G02B 21/0012* (2013.01)

(58) Field of Classification Search
CPC .... A61B 2018/2272; A61B 2018/2277; A61B 2018/00571; A61B 2018/00577; G02B 7/00; G02B 7/003; G02B 7/006; G02B 7/02; G02B 7/021; G02B 7/022; G02B 7/18; G02B 7/182; G02B 7/1872; G02B 7/20; G02B 21/00; G02B 21/0004; G02B 21/0012; G02B 21/0028; G02B 21/0032; G02B 21/0052; G02B 27/10; G02B 27/1006; G02B 27/106; B23K 26/08; B23K 26/083; B23K 26/0853; B23K 26/0861
USPC .................................. 606/4–6, 8–13, 17–19
See application file for complete search history.

(56) References Cited

U.S. PATENT DOCUMENTS

| | | | |
|---|---|---|---|
| 5,923,480 A | 7/1999 | Labeye | |
| RE37,185 E * | 5/2001 | Satoh | G11B 7/0045 369/275.3 |
| 6,462,814 B1 | 10/2002 | Lo | |
| 6,495,812 B1 * | 12/2002 | Wurm | G02B 7/28 204/461 |
| 6,873,640 B2 | 3/2005 | Bradburn et al. | |
| 2006/0056017 A1 | 3/2006 | Berier et al. | |
| 2007/0106285 A1 * | 5/2007 | Raksi | A61F 9/008 606/17 |
| 2007/0229946 A1 * | 10/2007 | Okada | G01N 21/6458 359/385 |
| 2008/0198485 A1 * | 8/2008 | Kosmowski | B23K 26/0876 359/811 |
| 2012/0307512 A1 | 12/2012 | Cogger et al. | |
| 2013/0319985 A1 | 12/2013 | Nomaru | |
| 2015/0165552 A1 * | 6/2015 | Sukhman | B23K 26/048 219/121.74 |

OTHER PUBLICATIONS

T. Karu, "Lasers in Infertility Treatment: Irradiation of Oocytes and Spermatozoa", *Photomedicine and Laser Surgery*, vol. 30, No. 5, pp. 239-241 (May 1, 2012).
"High-Performance Low-Profile Ball Bearing Linear Stages", *The Newport Resource 2006/2007 CD*, pp. 873-874 (Jan. 1, 2006).
K. Svoboda et al., "Biological Applications of Optical Forces", *Annual Review of Biophysics and Biomolecular Structure*, vol. 23, No. 1, pp. 247-285 (Jun. 1, 1994).
Bedient et al., "Laser Pulse Application in IVF", *Lasers—Applications in Science and Industry*, by Dr. Krzysztof Jakubczak (Ed.), pp. 193-214 (Dec. 2011).
"How Does Laser Cutting Work?", ESAB Knowledge Center, http://www.esabna.com/us/en/education/blog/how-does-laser-cutting-work.cfm, (Jul. 29, 2013).
Saturn 5TM Laser System User Manual, Research Instruments Ltd., Document 6-47-500UM, Issue 10 (Mar. 26, 2015).

* cited by examiner

LASER SYSTEMS AND RELATED METHODS

CROSS-REFERENCE TO RELATED APPLICATION

This application claims priority to U.S. Provisional Patent Application No. 62/325,085, filed on Apr. 20, 2016, the entire contents of which is incorporated herein by reference.

TECHNICAL FIELD

This disclosure relates to laser systems and related methods.

BACKGROUND

Laser systems (e.g., laser ablation systems) are used in the field of assisted reproductive technology (ART) to facilitate the process of in vitro fertilization (IVF), which involves fertilization of an oocyte by a sperm cell outside of the body. In order for fertilization to occur, the sperm cell must penetrate an outer glycoprotein layer (i.e., the zona pellucida) surrounding the oocyte. During the process of IVF, a laser system may be used to immobilize the sperm cell or to create a hole in the zona pellucida of the oocyte for facilitating injection of the sperm cell into the oocyte. Fertilization of the oocyte by the sperm cell results in an embryo that undergoes successive cell divisions. In order to implant itself on a uterine wall, the multicellular embryo must escape the zona pellucida in a process known as hatching. In some examples, a laser system may be used to create a hole in or thin a section of the zona pellucida to facilitate hatching. Additionally, a laser system may be used to create a hole in the zona pellucida for removal of one or more cells or cellular components from the embryo for various pre-implantation diagnostic or surgical procedures or for removal of fluid from the embryo prior to cryopreservation of the embryo.

SUMMARY

In general, this disclosure relates to laser ablation systems used in the field of assisted reproductive technology (ART). Such laser ablation systems can be used to create a hole in or thin a user-defined section of a structure of a cellular sample (e.g., a zona pellucida surrounding an oocyte or an embryo) or to immobilize a gamete (e.g., a sperm cell) during various stages of in vitro fertilization (IVF) or other ART procedures.

In one aspect, a laser system includes a collimator configured to output a collimated laser beam, a support member to which the collimator is mounted, and a linear rail along which the support member is movable in a first dimension such that the collimator, mounted to the support member, and the collimated laser beam, outputted from the collimator, are movable in the first dimension. The laser system further includes a lens positioned downstream of the collimator and configured to direct the collimated laser beam to a target location on a specimen.

In some embodiments, the laser system further includes an infrared laser configured to generate an infrared laser beam including infrared light waves with wavelengths in a range of about 700 nm to about 1 mm.

In some certain, the infrared laser is configured to generate an infrared laser beam including infrared light waves with wavelengths in a range of about 700 nm to about 2000 nm In some embodiments, the infrared light waves have a wavelength of about 1480 nm.

In certain embodiments, the laser system further includes a red laser configured to generate a red laser beam including red light waves with wavelengths in a range of about 620 nm to about 700 nm.

In certain embodiments, the red light waves have a wavelength of about 650 nm.

In some embodiments, the laser system further includes a set of optical components configured to combine the infrared laser beam and the red laser beam into one laser beam.

In certain embodiments, the collimator is configured to receive the one laser beam as a divergent laser beam and to output the divergent laser beam as the collimated laser beam.

In some embodiments, the laser system further includes a control module configured to activate the infrared laser such that the collimated laser beam, carrying the infrared light waves, can produce a hole in a structure of the specimen at the target location.

In certain embodiments, the specimen is an embryo, and the structure of the specimen is a zona pellucida of the embryo.

In some embodiments, the laser system further includes system software by which a user can select the target location and instruct the control module to activate the infrared laser.

In certain embodiments, the laser system further includes a fiber optic cable configured to carry the one laser beam to the collimator.

In some embodiments, the laser system is configured to produce an image of the specimen upon interaction of the red light waves with the specimen.

In certain embodiments, the linear rail defines a rectangular recess.

In some embodiments, the support member defines a corresponding rectangular recess.

In certain embodiments, the laser system further includes a ball bearing configured to slide simultaneously within the rectangular recess of the linear rail and within the corresponding rectangular recess of the support member to movably couple the support member to the linear rail.

In some embodiments, the support member is a first support member and the linear rail is a first linear rail, the laser system further including a second support member to which the first support member is mounted and a second linear rail along which the second support member is movable in a second dimension that is orthogonal to the first dimension such that the first support member, the collimator supported thereon, and the collimated laser beam outputted from the collimator, are movable in the second dimension.

In certain embodiments, the laser system further includes a motor configured to move the support member along the linear rail.

In some embodiments, the lens is configured to refract the collimated laser beam towards a central axis of the lens when the collimated laser beam is outputted from the collimator at a position spaced apart from the central axis of the lens.

In certain embodiments, the laser system further includes a microscope objective positioned downstream of the lens and configured to capture the collimated laser beam and to focus infrared light waves and visible light waves within the collimated laser beam at a same plane within the specimen.

In some embodiments, the laser system further includes a dichroic mirror configured to reflect infrared light waves within the collimated laser beam, to reflect a first portion of visible light waves within the collimated laser beam, and to transmit a second portion of the visible light waves within the collimated laser beam.

In certain embodiments, the dichroic mirror is positioned in a fixed orientation with respect to the lens.

In some embodiments, the laser system further includes a filter configured to block transmission of infrared light waves within the collimated laser beam.

In another aspect, a method of ablating a structure on a specimen includes moving a support member in a first dimension along a linear rail, the support member carrying a collimator outputting a collimated laser beam, and using a lens positioned downstream of the collimator, directing the collimated laser beam to a target location on a specimen.

In some embodiments, the method further includes generating an infrared laser beam including infrared light waves with wavelengths in a range of about 700 nm to about 1 mm.

In certain embodiments, the method further includes generating an infrared laser beam including infrared light waves with wavelengths in a range of about 700 nm to about 2000 nm.

In some embodiments, the infrared light waves have a wavelength of about 1480 nm.

In certain embodiments, the method further includes generating a red laser beam including red light waves with wavelengths in a range of about 620 nm to about 700 nm.

In certain embodiments, the red light waves have a wavelength of about 650 nm.

In some embodiments, the method further includes combining the infrared laser beam and the red laser beam into one laser beam.

In certain embodiments, the collimator is configured to receive the one laser beam as a divergent beam and to output the divergent laser beam as the collimated laser beam.

In some embodiments, the method further includes activating the infrared laser such that the collimated laser beam, carrying the infrared light waves, produces a hole in a structure of the specimen at the target location.

In certain embodiments, the specimen is an embryo, and the structure of the specimen is a zona pellucida of the embryo.

In some embodiments, the method further includes receiving a selection of the target location via system software and instructing the control module to activate the infrared laser.

In certain embodiments, the method further includes carrying the one laser beam to the collimator.

In some embodiments, the method further includes producing an image of the specimen upon interaction of the red light waves with the specimen.

In certain embodiments, the linear rail defines a rectangular recess.

In some embodiments, the support member defines a corresponding rectangular recess.

In certain embodiments, the method further includes moving a ball bearing simultaneously within the rectangular recess of the linear rail and within the corresponding rectangular recess of the support member to movably couple the support member to the linear rail.

In some embodiments, the support member is a first support member and the linear rail is a first linear rail, the method further including moving a second support member in a second dimension along a second linear rail, the second dimension being orthogonal to the first dimension, and the second support member carrying the first support member, such that the collimator, mounted thereon, and the collimated laser beam, outputted from the collimator, are movable in the second direction.

In certain embodiments, the support member is moved along the linear rail by a motor.

In some embodiments, the lens is configured to refract the collimated laser beam towards a central axis of the lens when the collimated laser beam is outputted from the collimator at a position spaced apart from the central axis of the lens.

In certain embodiments, the method further includes capturing the collimated laser beam in a microscope objective positioned downstream of the lens and focusing infrared light waves and visible light waves within the collimated laser beam at a same plane within the specimen.

In some embodiments, the method further includes reflecting infrared light waves within the collimated laser beam with a dichroic mirror, reflecting a first portion of visible light waves within the collimated laser beam with the dichroic mirror, and transmitting a second portion of the visible light waves within the collimated laser beam with the dichroic mirror.

In certain embodiments, the dichroic mirror is positioned in a fixed orientation with respect to the lens.

In some embodiments, the method further includes blocking transmission of infrared light waves within the collimated laser beam using an infrared filter.

Embodiments may provide one or more of the following advantages.

A compact size and configuration of a motor module of the laser system can make the laser system suitable for use with microscopes and other standard equipment typically used in IVF and other ART procedures.

Additionally, rectangular-shaped recesses within support blocks of the motor module and within associated vertical and horizontal linear rails can result in straight (e.g., linear) slide features that facilitate manufacturing of the support blocks and the vertical and horizontal linear rails (e.g., production of these components with required accuracies), as compared to more difficult manufacturing requirements that must be achieved to produce motor module components in other laser systems that include movement slides with curved features.

Due to the refractive capabilities of a scanning lens of the laser system, the scanning lens can, in some embodiments, direct the moving collimated beam to a desired position along the optical path of the laser system without movement of the dichroic mirror (i.e., the dichroic mirror is positioned in a fixed location and a fixed orientation with respect to the scanning lens along the optical path). Avoiding such movement of the dichroic mirror can simplify operation of the laser system, as compared to other laser systems (e.g., confocal scanning microscopes) that require oscillation or other movement of a dichroic mirror for desired targeting of a laser beam.

Other aspects, features, and advantages will be apparent from the description, the drawings, and the claims.

DETAILED DESCRIPTION

Figure 1:
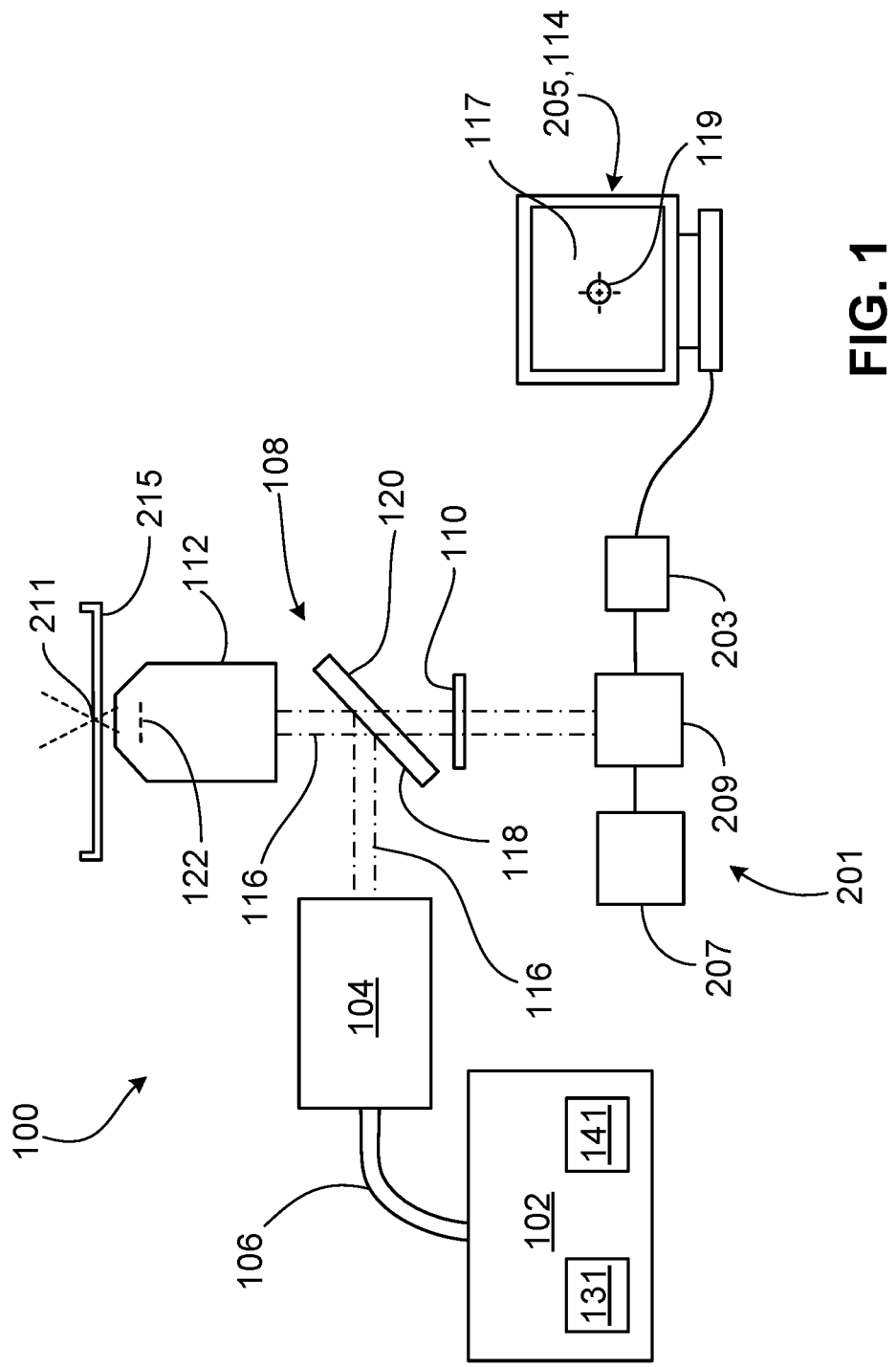
FIG. 1 is a diagram of a laser system assembled with a microscope.

FIG. 1 shows a diagram of a laser system 100 adapted for use in the field of assisted reproductive technology (ART). The laser system 100 is assembled with a microscope 201, a video camera 203, and a computer 205 to ablate or to thin a user-defined section of a gamete or an embryo (e.g., a portion of a zona pellucida of an oocyte or an embryo or a tail of a sperm cell) for facilitating fertilization of the oocyte by the sperm cell or for facilitating hatching, biopsy, or collapse of the embryo during various stages of an in vitro fertilization (IVF) process. In some examples, the laser system 100, assembled with the microscope 201, the video camera 203, and the computer 205, can be used to perform other microsurgical procedures on the embryo. The microscope 201 shown in FIG. 1 is an inverted microscope that includes, among other standard microscope components, eyepieces 207 through which a user can view a specimen 211 and a prism 209 that directs light transmitted through the specimen 211 to the eyepieces 207 and to the video camera 203 for visualization of the specimen 211.

The laser system 100 includes a control module 102, a motor module 104, a fiber optic cable 106 (e.g., a fiber optic patch lead), a dichroic mirror 108, an infrared (IR) filter 110, and an objective 112 that cooperate to deliver a laser beam to a target position on the specimen 211. The laser system 100 also includes system software 114 (e.g., a viewer software) that is installed on the computer 205 and that provides various user-interfaces through which the user can provide instructions for operation of the laser system 100.

The control module 102 includes an infrared laser 131 (e.g., an ablation laser) and a red laser 141 (e.g., a targeting laser). The infrared laser 131 emits a laser beam that has a wavelength in a range of about 700 nm to about 1 mm (e.g., 1480 nm), while the red laser 141 emits a laser beam that has a wavelength in the visible light range of about 620 nm to about 700 nm (e.g., 650 nm). The control module 102 also includes electronics that control power outputs and activation of the lasers 131, 141, as well as fiber optic components that combine the two laser beams into one fiber beam (e.g., a beam including light rays traveling parallel to one another along parallel fiber optic components) carrying both the infrared energy and the red energy. The fiber optic components direct the fiber beam out of the control module 102 for transmission into the fiber optic cable 106. As the fiber beam exits the fiber optic components of the control module 102, the fiber beam takes the form of a divergent beam (e.g., a beam including light rays traveling in different directions from a beam source). The control module 102 is typically placed (e.g., on a workbench) within close proximity to the microscope 201 (e.g., about 1.0 m to about 2.0 m from the microscope 201).

The fiber optic cable 106 receives the divergent beam from the control module 102, and the divergent beam takes the form of a fiber beam within the fiber optic cable 106. The fiber optic cable 106 includes a flexible, metal (e.g., stainless steel) jacket that protects the fiber beam. The fiber optic cable 106 typically has a length of about 1.0 m to about 2.0 m (e.g., 1.5 m) and is configured for optimal transmission of the fiber beam from the control module 102 to the motor module 104. The fiber beam again becomes a divergent beam as the fiber beam exits the fiber optic cable 106. The motor module 104 is configured to receive the divergent beam exiting the fiber optic cable 106, to collimate the divergent beam to form a collimated beam 116 (e.g., a beam including light rays directed parallel to one another), and to direct the collimated beam 116 to the dichroic mirror 108, as will be discussed in more detail below with respect to FIGS. 2-6.

The dichroic mirror 108 includes a forward surface 118 (e.g., facing the motor module 104) that reflects about 100% of the infrared energy (e.g., the light rays with wavelengths in the range of about 700 nm to about 2 mm) within the collimated beam 116 towards the objective 112. The forward surface 118 typically reflects about 50% of the red energy (e.g., light rays with wavelengths in a range of about 620 nm to about 700 nm) within the collimated beam 116 towards the objective 112 and transmits (e.g., passes) the remaining red energy (e.g., light rays with wavelengths in a range of about 620 nm to about 700 nm) within the collimated beam 116. The forward surface 118 of the dichroic mirror 108 also transmits visible light (e.g., light rays with a wavelength of about 400 nm to about 700 nm) reflected from the specimen 211 to a rearward surface 120 of the dichroic mirror 108. In some cases, the forward surface 118 is coated with one or more thin film optical coatings, which may contribute to the light transmission and light reflective properties of the forward surface 118. In some cases, the rearward surface 120 is coated with one or more thin films anti-reflection coatings, which may contribute to the transmission of the reflected visible light to the prism 209 of the microscope 201. While the dichroic mirror 108 is illustrated as oriented in arbitrary angles in FIGS. 1, 7, and 8, in some embodiments, the dichroic mirror 108 is orientated at an angle of about 30° to about 60° (e.g., about 45°) from a central axis of the scanning lens 130. Accordingly, the dichroic mirror 108 is orientated at an angle of about 30° to about 60° (e.g., about 45°) from a central axis of the objective 112.

The IR filter 110 is positioned between the dichroic mirror 108 and the prism 209 to block any small amount of infrared light (e.g., reflected from the specimen 211, reflected from a sample container supporting the specimen 211, or transmitted from the motor module 104) that manages to pass through the forward and rearward surfaces 118, 120 of the dichroic mirror 108 such that the infrared light is prevented from passing into the eyepieces 207 and therefore reaching the user's eyes. Light entering the prism 209 is refracted and directed to both the eyepieces 207 for visualization of the specimen 211 and to the video camera 203 for image and/or video capture of the specimen 211. Images and videos captured by the video camera 203 are displayed on a user interface provided by the system software 114 on a monitor of the computer 205, as will be discussed in more detail below with respect to a field of view 117 and a cross-hair 119 displayed on the user interface.

The objective 112 is a custom objective configured to receive the collimated beam 116 in an entrance pupil 122 of the objective 112 and to focus the infrared light and the visible light within the collimated beam 116 at the same plane within the specimen 211. Accordingly, the user simply needs to focus the visible light at a desired plane within the specimen 211, and such focusing will also result in focusing of the infrared light at the same plane. Furthermore, the objective 112 is configured to increase (e.g., maximize) transmission of the infrared light in the collimated beam 116 to the specimen 211. The objective 112 can, for example, transmit as high a portion of infrared energy as possible. In contrast, standard microscope objectives are typically only capable of focusing visible light or light just outside of the visible range. In this regard, the objective 112 provides optical features not achievable by many standard microscope objectives that are not able to focus infrared light and visible light at the same plane. Such attempted focusing with a standard microscope objective would generally result in a loss of a large portion of infrared energy due to back-reflection and absorption.

Figure 2:
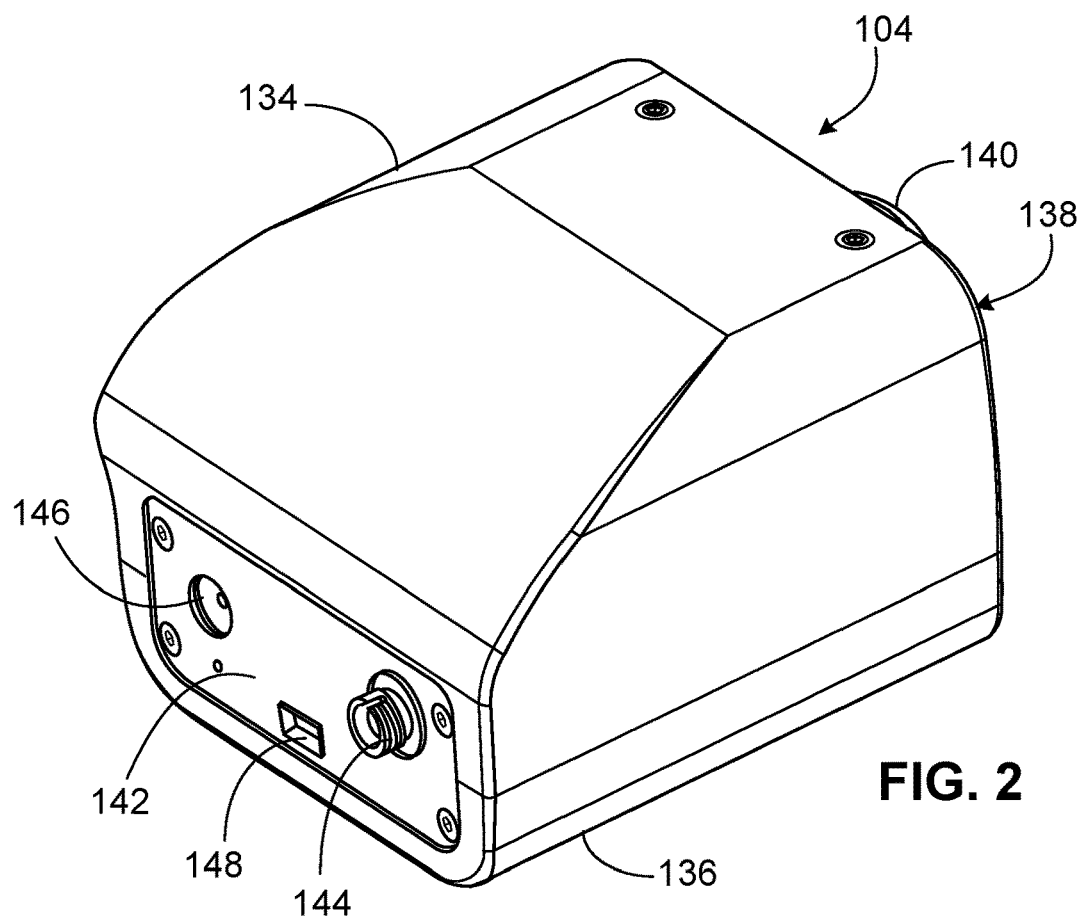
FIG. 2 is a rear perspective view of a motor module of the laser system of FIG. 1.
Figure 3:
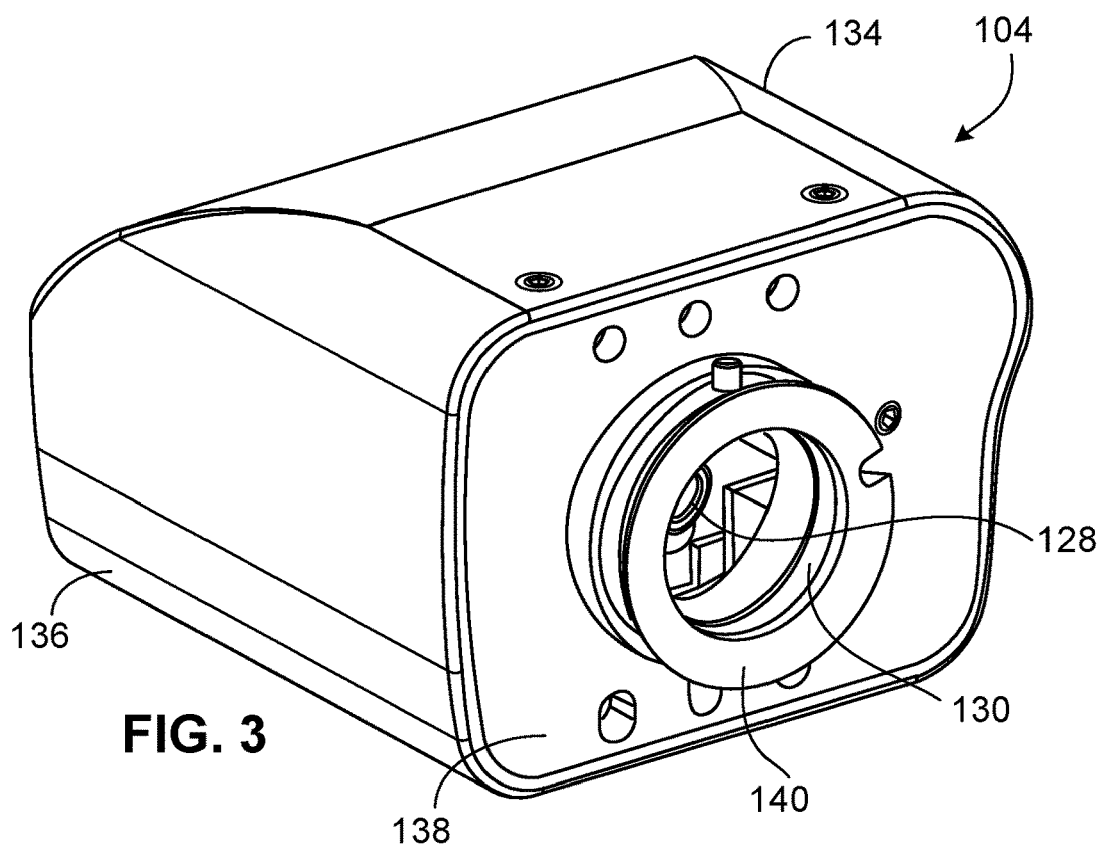
FIG. 3 is a front perspective view of the motor module of FIG. 2.
Figure 4:
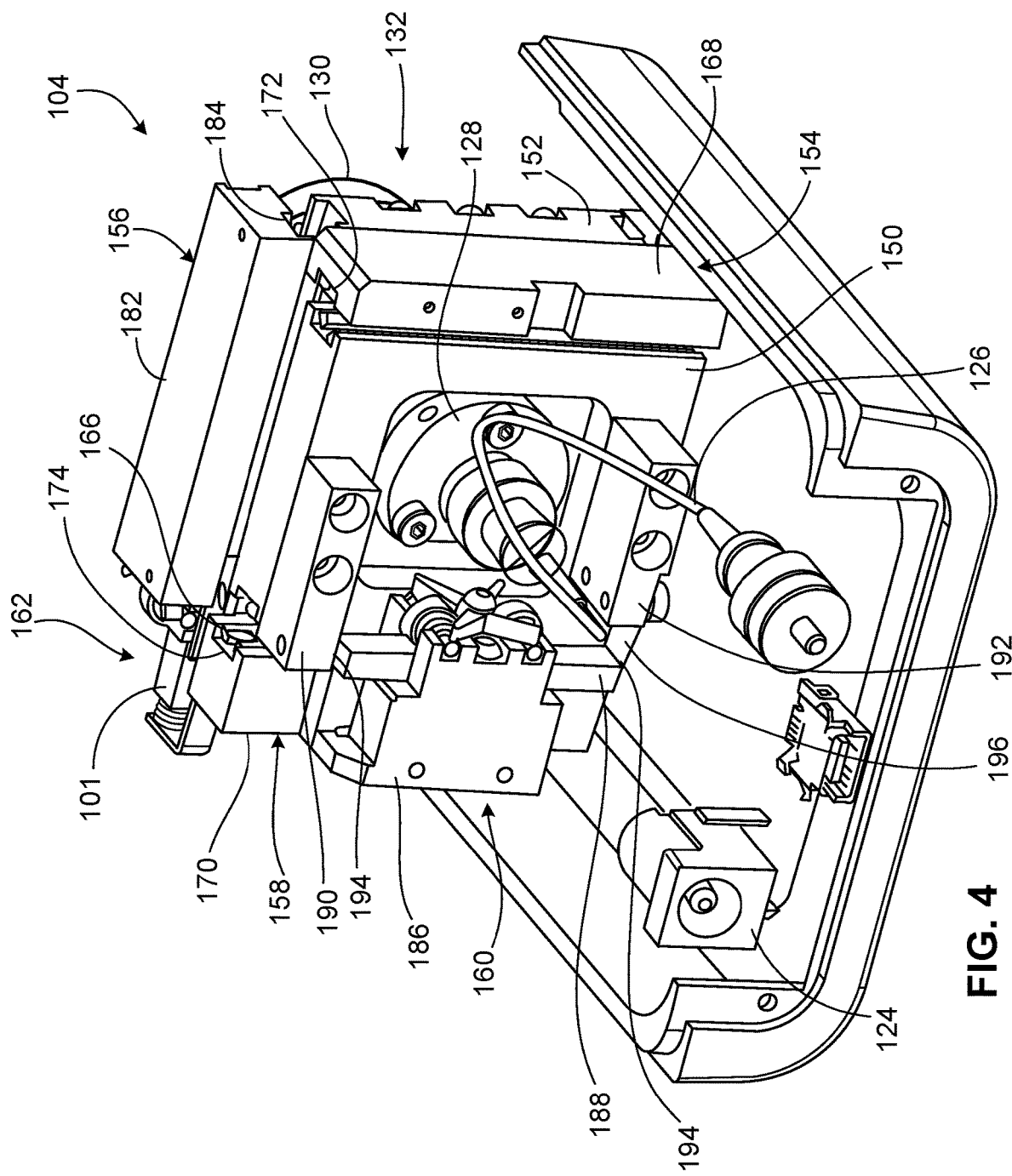
FIG. 4 is a rear perspective view of the motor module of FIG. 2 with various components omitted for visualization of certain internal components.
Figure 5:
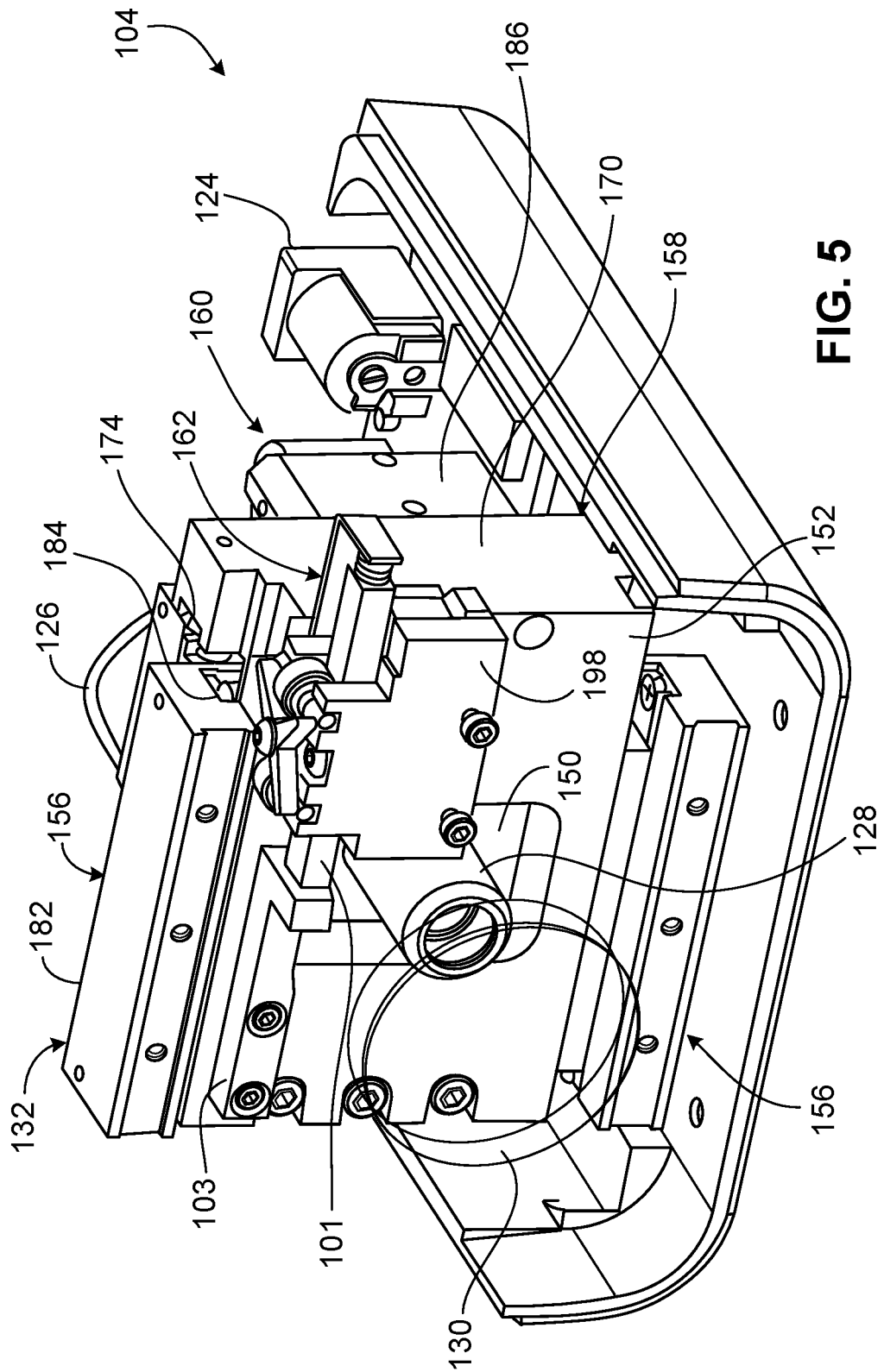
FIG. 5 is a front perspective view of the motor module of FIG. 2 with various components omitted for visualization of certain internal components.
Figure 6:
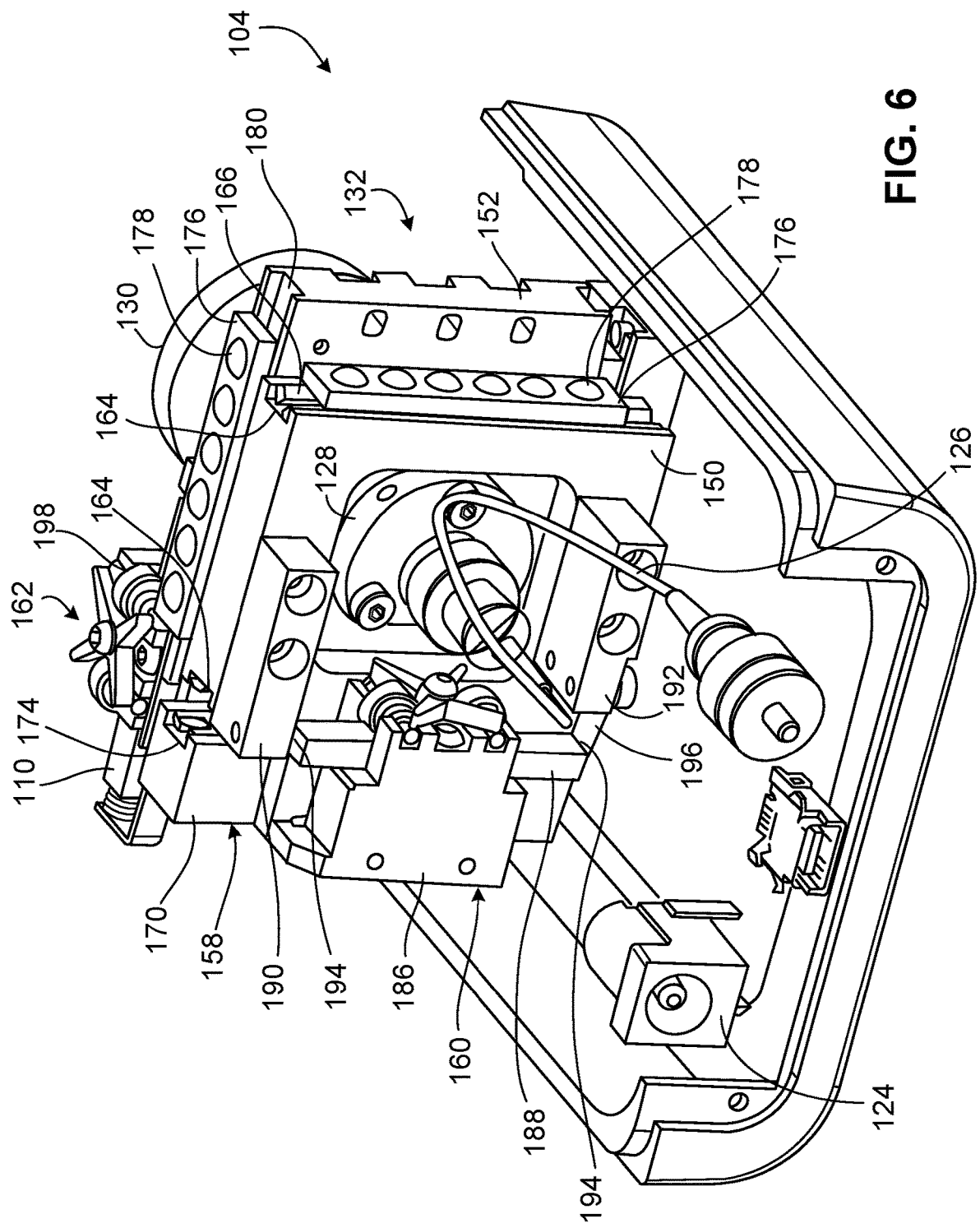
FIG. 6 is a rear perspective view of the motor module of FIG. 2 with various components omitted for visualization of certain internal components.

FIGS. 2-6 illustrate various perspective views of the motor module 104. Certain components of the motor module 104 are omitted in FIGS. 4-6 in order to expose internal components. The motor module 104 is adapted to receive the divergent beam exiting the fiber optic cable 106, to collimate the divergent beam to form the collimated beam 116, to move the collimated beam 116 to a desired location according to the target location on the specimen 211, and to direct the collimated beam 116 to the dichroic mirror 108. Referring particularly to FIGS. 4-6, the motor module 104 includes a power socket 124 allowing the motor module 104 to be powered by a mains adapter, and a flexible internal fiber optic cable 126 (e.g., a fiber optic patch lead) that receives the divergent beam exiting the fiber optic cable 106. The divergent beam takes the form of a fiber beam within the fiber optic cable 126 and again becomes a divergent beam upon exiting the fiber optic cable 126. The motor module 104 also includes a collimator 128 that collimates the divergent beam exiting the fiber optic cable 126 to form the collimated beam 116, a scanning lens 130 that directs the collimated beam 116 to the dichroic mirror 108, and a beam positioning system 132 that moves the collimator 128 with respect to the scanning lens 130.

Referring to FIGS. 2 and 3, the internal components of the motor module 104 are surrounded by an upper housing portion 134, a lower housing portion 136, a front panel 138 defining a lens support 140 through which the collimated beam 116 exits the motor module 104, and a rear panel 142. The rear panel 142 defines an opening supporting a connector 144 to which the fiber optic cables 106, 126 are attached, defines an opening 146 through which a power cable can be passed, and defines an opening 148 through which a USB cable can be inserted for transmitting commands from the computer 205 to the motor module 104.

Referring to FIGS. 4 and 5, the beam positioning system 132 includes a rear support block 150 to which the collimator 128 is mounted, a frontal support block 152 through which the collimator 128 extends, a vertical slide mechanism 154 by which the rear support block 150 moves vertically, and two horizontal slide mechanisms 156 by which the frontal support block 152 moves horizontally. The frontal support block 152 includes an integral vertical slide mechanism 158 by which the rear support block 150 moves vertically, in cooperation with the vertical slide mechanism 154. The beam positioning system 132 further includes a rear motor assembly 160 by which the rear support block 150 moves along the vertical slide mechanisms 154, 158 and a frontal motor assembly 162 by which the frontal support block 152 moves along the horizontal slide mechanisms 156.

Referring to FIGS. 4-6, the rear support block 150 defines rectangular recesses 164 along opposing sides into which two ball tracks 166 are set. The vertical slide mechanisms 154, 156 include vertical bars 168, 170 that also define rectangular recesses 172, 174 into which two ball tracks 166 are set. Each vertical slide mechanism 154, 156 further includes a ball cage 176 and associated ball bearings 178 that are rollable along the ball tracks 166 in the rectangular recesses 164, 172, 174 as the rear support block 150 is translated vertically by the rear motor assembly 160. Along upper and lower sides, the frontal support block 152 defines rectangular recesses 180 into which two ball tracks 166 are set. Each horizontal slide mechanism 156 is attached to the front panel 138 and includes horizontal bars 182 that also define rectangular recesses 184 into which two ball tracks 166 are set. Each horizontal slide mechanism 156 further includes a ball cage 176 and associated ball bearings 178 that are rollable along the ball tracks 166 in the rectangular recesses 184 as the frontal support block 152 is translated horizontally by the frontal motor assembly 162.

In some embodiments, the rear support block 150 has a height of about 0.6 cm to about 1.0 cm (e.g., about 0.8 cm), a length of about 3.0 cm to about 5.0 cm (e.g., about 4.0 cm), and a width of about 3.0 cm to about 4.0 cm (e.g., about 3.2 cm). The recesses 164 have a width of about 4.0 mm to about 6.0 mm (e.g., about 5.0 mm) and a depth of about 1.0 mm to about 2.0 mm (e.g., about 1.5 mm). In some embodiments, the frontal support block 152 has a height of about 1.0 cm to about 2.0 cm (e.g., about 1.7 cm), a length of about 4.0 cm to about 6.0 cm (e.g., about 5.0 cm), and a width of about 3.0 cm to about 4.0 cm (e.g., about 3.5 cm). The recesses 180 have about the same width and about the same depth as the recesses 164. In some embodiments, the vertical and horizontal bars 168, 170, 182 have a length of about 3.0 cm to about 5.0 cm (e.g., about 4.0 cm), and the recesses 172, 174, 184 have about the same width and about the same depth as the recesses 164, 180. In some embodiments, the ball cages 176 have a length of about 3.0 cm to about 5.0 cm (e.g., about 4.0 cm), a width of about 0.4 cm to about 0.8 cm (e.g., about 0.6 cm), and a thickness of about 0.1 cm to about 0.3 cm (e.g., about 0.2 cm). In some embodiments, the length of the internal fiber optic cable 126 is about 10.0 cm to about 20.0 cm (e.g., about 16.0 cm). In some embodiments, the upper and lower housing portions 134, 136 have a length of about 6.0 cm to about 10.0 cm (e.g., about 8.0 cm) and a width of about 7.0 cm to about 10.0 cm (e.g., about 8.0 cm). In some embodiments, the motor module 104 has a maximum height of about 5.0 cm to about 8.0 cm (e.g., about 6.0 cm). A compact size and configuration of the motor module 104 makes the laser system 100 suitable for use with microscopes (e.g., the microscope 201) and other standard equipment typically used in IVF and other ART procedures.

In some embodiments, the support blocks 150, 152, the vertical and horizontal bars 168, 170, the ball cages 176, the housing portions 134, 136, the rear panel 142, and the front panel 138 are made of one or more materials including metals, such as aluminum (e.g. Al 6082T6 or Al 5251-H22), polycarbonate, or other polymers and may be coated with one or more materials including anodized aluminum oxide, or paint. In some embodiments, the support blocks 150, 152, the vertical and horizontal bars, the housing portions 134, 136, the rear panel 142, and the front panel 138 are manufactured via milling, casting, or metal laser sintering. Selection of rectangular-shaped recesses 164, 172, 174, 180, 184 within the support blocks 150, 152 and within the vertical and horizontal bars 168, 170, 182 results in straight (e.g., linear) slide features that facilitate manufacturing of the support blocks 150, 152 and the vertical and horizontal bars 168, 170, 182 (e.g., production of these components with required accuracies), as compared to more difficult manufacturing requirements that must be achieved to produce motor module components in other laser systems that include movement slides with curved features.

Still referring to FIGS. 4-6, the rear motor assembly 160 includes a rear motor 186 (e.g., a piezoelectric linear motor) that is attached to the integrated vertical slide mechanism 158, a vertical drive bar 188 that is translatable vertically by the rear motor 186, upper and lower movement blocks 190, 192 that are attached to the rear support block 150, detent balls 194 that connect the upper and lower movement blocks 190, 192 to the vertical drive bar 188 and to a connector plate 196 that is connected the lower movement block 192. In some embodiments, the vertical drive bar 188 has a height of about 2.0 cm to about 4.0 cm (e.g., about 3.0 cm) and is moveable vertically (e.g., thereby moving the rear support block 150) by about 1.0 cm to about 2.0 cm. The frontal motor assembly 162 includes a frontal motor 198 (e.g., a piezoelectric linear motor) that is attached to the frontal support block 152, a horizontal drive bar 101 that is translatable horizontally by the frontal motor 198, and a movement block 103 that is attached to the frontal support block 152. In some embodiments, the horizontal drive bar 101 has a length of about 2.0 cm to about 4.0 cm (e.g., about 3.0 cm) and is movable horizontally (e.g., thereby moving the frontal support block 152) by about 1.0 cm to about 2.0 cm.

In some embodiments, the drive bars 101, 188 and the movement blocks 103, 190, 192 are made of one or more materials including metals, such as aluminum (e.g. Al 6082T6 or Al 5251-H22), polycarbonate, or ceramic and may be coated with one or more materials including anodized aluminum oxide, or paint. In some embodiments, the drive bars 101, 188 and the movement blocks 103, 190, 192 are manufactured via milling, casting. or metal laser sintering.

It should be understood that the laser system 100 includes other standard electrical and mechanical components (e.g., circuitry components, power components, mechanical fasteners, and mechanical support members) involved in the functioning of the laser system 100.

Figure 7:
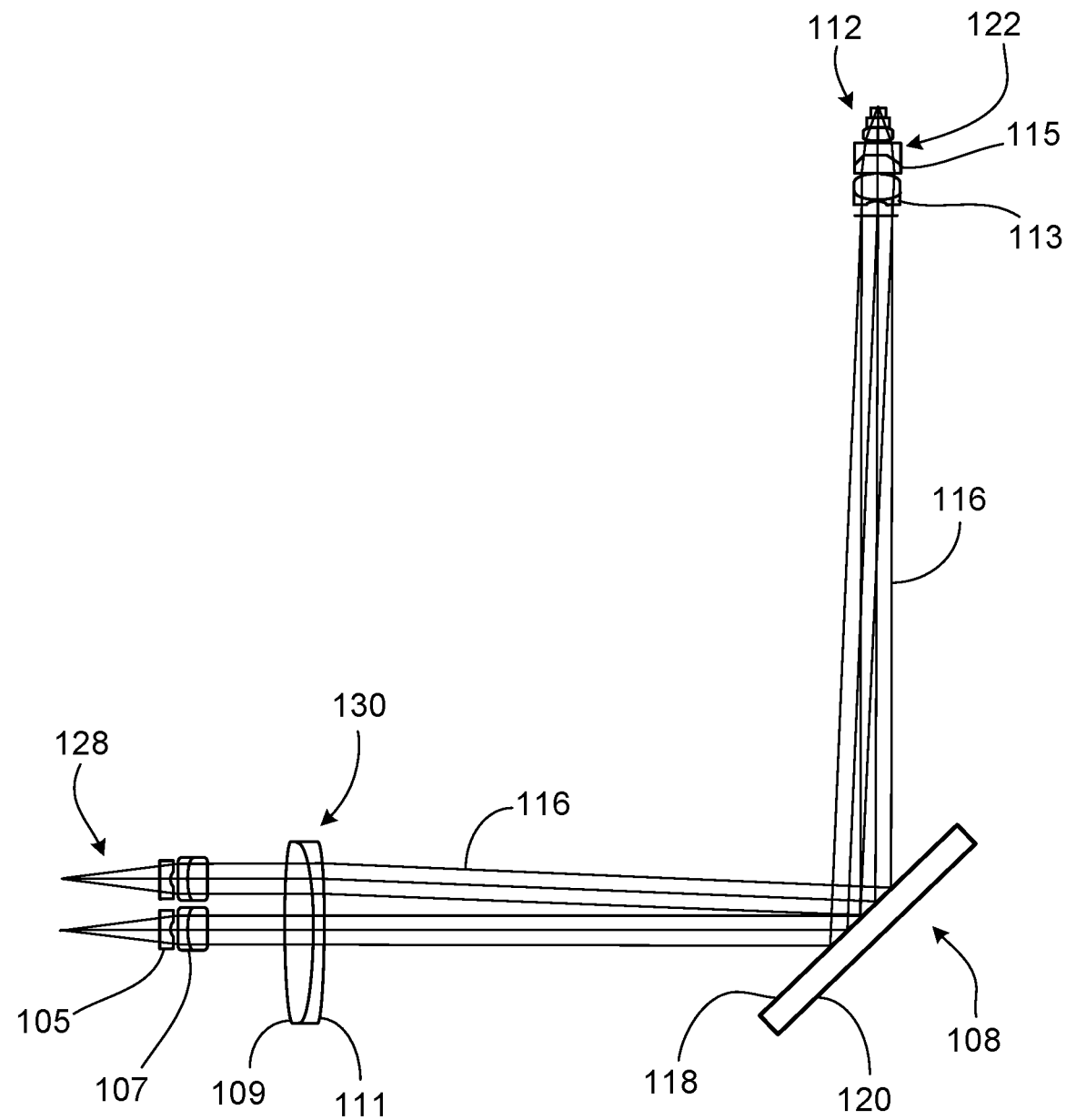
FIG. 7 is a diagram of various lenses within the laser system of FIG. 1.

FIG. 7 illustrates a diagram of the various lenses within the laser system 100. The collimator 128 includes a first lens 105 (e.g., a singlet) and a second lens 107 (e.g., a doublet) that cooperate to collimate the divergent beam received from the control module 102. As discussed above, the collimator 128 can be moved in two different dimensions. The lens 105, 107 are shown in two different positions of the collimator 128 for illustration purposes. The scanning lens 130 is a doublet with a first (left) bevel 109 and a second (right) bevel 111 that provide easy distinction of one side of the scanning lens 130 from the other side of the scanning lens 130. The scanning lens 130 refracts the collimated beam 116 such that the collimated beam 116 is directed to the entrance pupil 122 of the objective 112. The objective 112 includes two lenses 113, 115 (e.g., doublets) that focus the collimated beam 116 onto the specimen 211.

In some embodiments, the first and second lenses 105, 107 of the collimator 128 respectively have diameters of about 5.0 mm to about 6.0 mm (e.g., about 5.5 mm) and about 5.0 mm to about 7.0 mm (e.g., about 6.0 mm). In some embodiments, a distance between the internal fiber and the first lens 105 of the collimator 128 is about 10.0 mm to about 15.0 mm (e.g., about 13.9 mm). In some embodiments, a distance between the first and second lenses 105, 107 of the collimator 128 is about 0.5 mm to about 3.0 mm (e.g., about 0.6 mm). In some embodiments, the scanning lens 130 has a diameter of about 20.0 mm to about 30.0 mm (e.g., about 25.0 mm). In some embodiments, the first bevel 109 of the scanning lens 130 has a length of about 0.5 mm to about 1.5 mm (e.g., about 1.1 mm), and the second bevel 111 of the scanning lens 130 has a length of about 0 mm to about 0.5 mm (e.g., about 0.3 mm). In some embodiments, a distance between the second lens 107 of the collimator 128 and the scanning lens 130 is about 8.0 mm to about 14.0 mm (e.g., about 11.0 mm). In some embodiments, a total distance between the scanning lens 130 and the entrance pupil 122 of the objective 112 (e.g., a total distance along the optical path, including the dichroic mirror 108) is about 160.0 mm to about 200.0 mm (e.g., about 171.9 mm). The collimator lenses 105, 107, the scanning lens 130, and the objective lenses 113, 115 may be made of one or more materials (e.g., optical glass or another type of glass).

Figure 8:
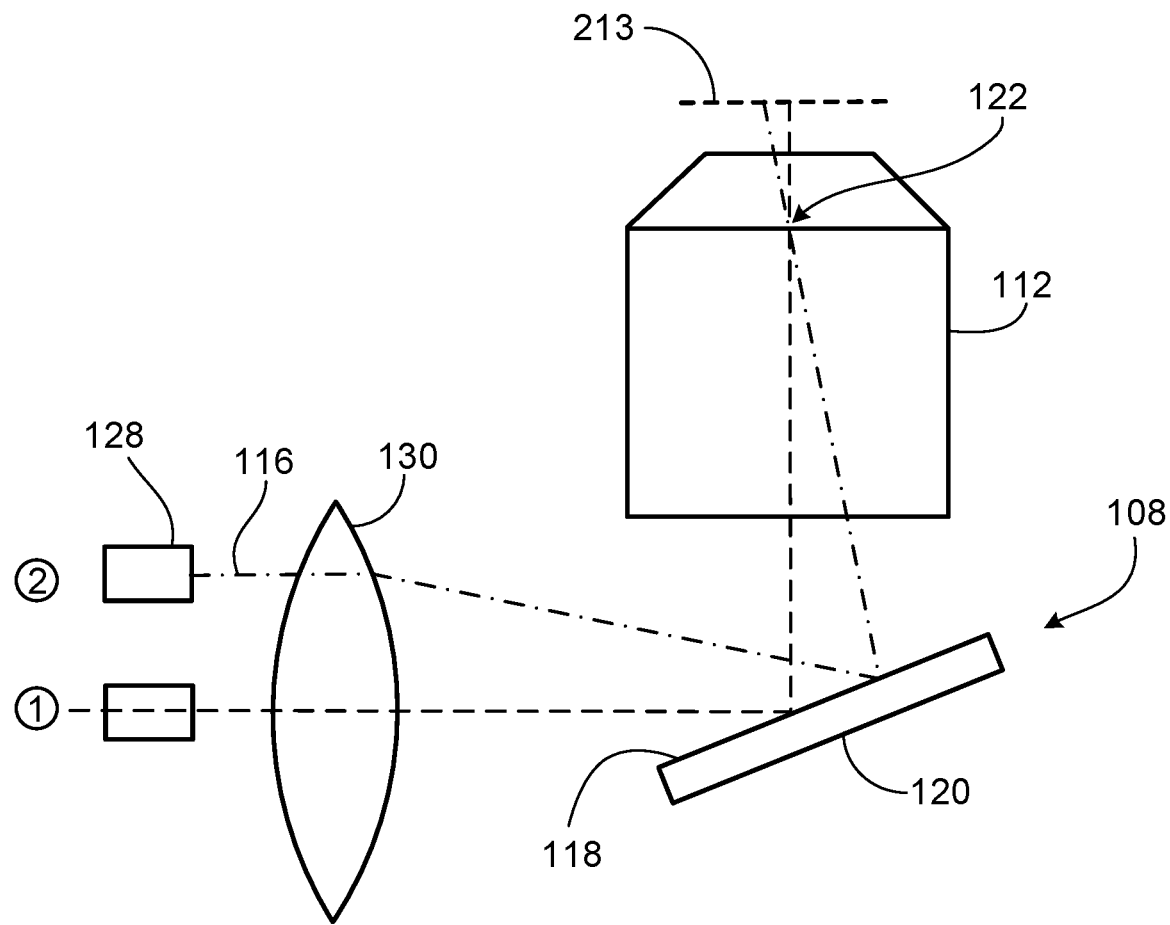
FIG. 8 is a diagram illustrating movement of a laser beam produced by the laser system of FIG. 1.

FIG. 8 shows a diagram illustrating movement of the collimated beam 116 as a function of movement of the collimator 128 in one dimension. At position 1, the collimator 128 is centrally aligned with the scanning lens 130, such that the collimated beam 116 (shown in dashed line) is transmitted along a central axis of the scanning lens 130, to an associated point on the dichroic mirror 108, along a central axis of the objective, and to a focal plane 213 on the specimen 211 without refraction of the collimated beam 116 by the scanning lens 130. At position 2, the collimator 128 is spaced apart from the central axis of the scanning lens 130, such that the collimated beam 116 (shown in dashed-dotted line) is refracted by the scanning lens 130 for direction to an associated point on the dichroic mirror 108 (omitted for clarity), into the entrance pupil 122 of the objective 112 and for transmission to the focal plane 213 from the entrance pupil 122.

As illustrated, moving the collimator 128 away from the central axis of the scanning lens 130 results in refraction of the collimated beam 116 by the scanning lens 130, which ensures that the collimated beam 116 is captured in the entrance pupil 122 of the objective 112 for focusing onto the specimen 211. Due to the refractive capabilities of the scanning lens 130, the scanning lens 130 is able to direct the moving collimated beam 116 to a desired position along the optical path of the laser system 100 without movement of the dichroic mirror 108 (i.e., the dichroic mirror 108 is positioned in a fixed location and a fixed orientation with respect to the scanning lens 130 along the optical path). Avoiding such movement of the dichroic mirror 108 simplifies operation of the laser system 100, as compared to other laser systems (e.g., confocal scanning microscopes) that require oscillation or other movement of a dichroic mirror for desired targeting of a laser beam. While movement of the collimator 128 is shown only in one dimension in FIG. 8, it should be understood that movement of the collimator 128 in a second, orthogonal dimension is characterized by the same principles as those illustrated in FIG. 8.

In operation, a user switches on the control module 102 of the laser system 100, causing the motor module 104 to undergo an initialization process during which a functional status of the motor assemblies 160, 162 are indicated by a bi-color (e.g., red/green) LED. If the LED indicates improper functioning of the motor assemblies 160, 162, then the control module 102 disables the motor controls for diagnosis and repair. If the LED indicates proper functioning of the motor assemblies 160, 162, then the user can start the computer 205 and the system software 114, such that the system software 114 is communicated with the control module 102 and the motor assemblies 160, 162 to display laser control functions in a user interface. The user then focuses the objective 112 on an empty sample container and performs a motor calibration procedure. The motor calibration procedure involves software-instructed movement of the motors 186, 198 to various positions and associated point identification on the user interface (e.g., via clicking) to map motor coordinates to screen pixels on the user interface.

Figure 9:
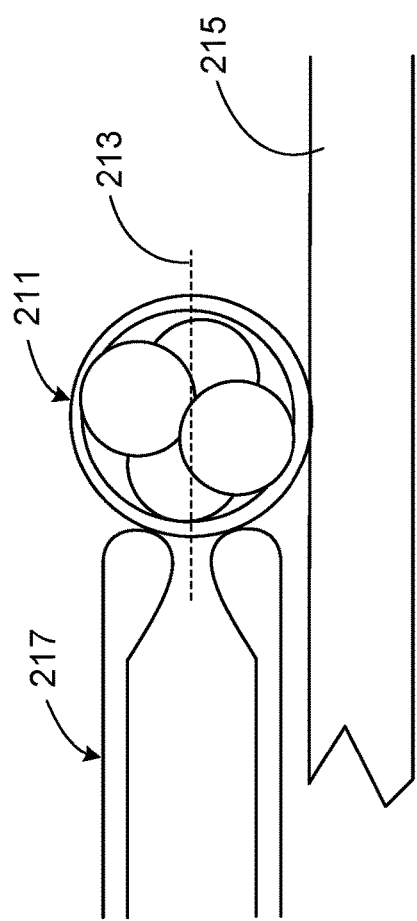
FIG. 9 is a side cross-sectional view of a specimen supported by a sample container on the microscope of FIG. 1.
Figure 11:
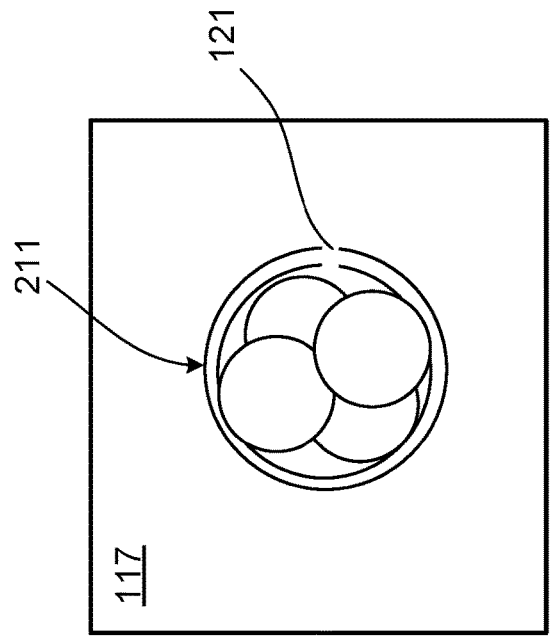
FIG. 11 is a top cross-sectional view of the specimen of FIG. 9 within the field of view of FIG. 10 and including a hole created by laser ablation at the location selected in FIG. 10.
Figure 10:
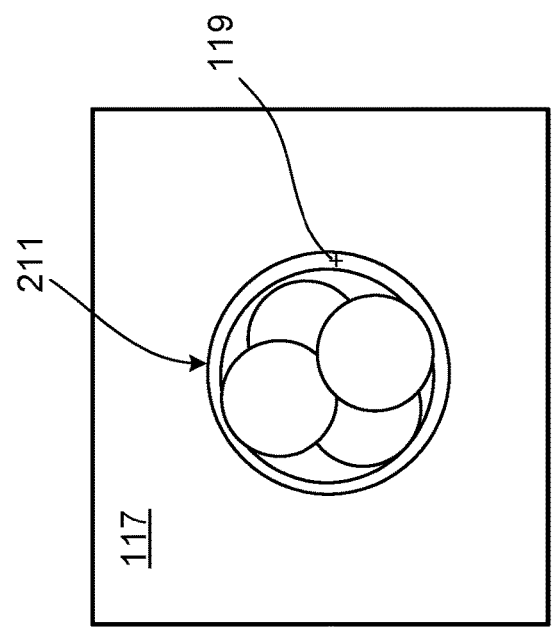
FIG. 10 is a top cross-sectional view of the specimen of FIG. 9 within a field of view with a location selected for laser ablation.

Referring to FIGS. 9-11, the user then places a sample container 215 (e.g., a petri dish) supporting the specimen 211 on a stage of the microscope 201, located directly above the objective 112. The user positions the container 215 in a field of view 117 (refer to FIG. 1) captured by the video camera 203 and displayed in the user interface and uses the objective 112 to focus on the plane 213 through the specimen 211 (i.e., a mid-plane of the specimen 211). In some cases, the user may then hold the specimen 211 in place on the bottom of the sample container 215 using a pipette. The user selects a target location on the specimen 211 (e.g., on the zone pellucida of an embryo) for laser ablation by moving an on-screen cross-hair 119 overlaying the field of view 117 displayed in the user interface. The user then provides a hole size for ablation at the target location using an on-screen selection tool (e.g., an adjustable bar, +/− buttons, or an entry field). The system software 114 calculates a laser pulse length (e.g., typically in a range of about 15 μs to about 1000 μs) required to form a hole of the selected size. The system software 114 displays a preview of the hole size on the user interface so that the user can change the selected hole size accordingly if desired. The system software 114 calculates motor coordinates using the coordinate mapping previously determined and instructs the motors 186, 198 to move via the vertical and horizontal slide mechanisms 154, 156, 158 to the chosen location.

Once the motors reach the target location, the system software 114 displays an activation (e.g., "Click to Fire") button on the user interface. The user then clicks the activation button, and the system software 114 instructs the control module 102 to fire the infrared laser at the calculated pulse duration to form a hole 121 in the specimen 211. In some examples, the hole 121 creates an opening in a structure of the specimen 211 (e.g., in a zona pellucida of an embryo). In some examples, the hole 121 is formed as a pocket that thins a structure of the specimen 211 (e.g., the zona pellucida of the embryo) without creating an opening through an entire cross-section of the structure. In some cases, the user instructs the system to fire additional laser pulses at the same target location or at a nearby location to enlarge the hole 121 formed in the structure or to further thin the structure. At any time during the procedure, the user can instruct the software to capture and/or store videos and/or still images of the specimen 211 in a data store of the computer 205. Once the user completes the procedure, the user closes the system software 114, powers off the computer 205, and then powers off the control module 102 of the laser system 100. The specimen 211 can subsequently be used in one or more desired IVF or other ART procedures according to standard protocols.

While certain embodiments have been described above, other embodiments are possible.

For example, in some embodiments, a laser system has component dimensions and component materials that differ from those mentioned above.

While the laser system 100 has been described as useable with an inverted microscope (e.g., the microscope 201), in some embodiments, the laser system 100 may be usable with upright microscopes.

While the laser system 100 has been described as including an infrared laser that emits a laser beam that has wavelengths in a range of about 700 nm to about 1 mm, in some embodiments, a laser system includes an infrared laser that emits a laser beam that has wavelengths in a range of about 700 nm to about 2000 nm.

While the scanning lens 130 has been described as a doublet made of optical glass, in some embodiments, a laser system includes a different type of scanning lens or a scanning lens made of a different type of glass to achieve optical effects similar to those discussed above with respect to the laser system 100.

While the laser system 100 has been described as including the ball cage 176 and the ball bearings 178 for coupling of the support blocks 150, 152, to the linear bars 168, 170, 182, in some embodiments, a laser system uses a different type of movement mechanism, such as flexural hinges to couple support blocks to linear bars of a motor module.

While the motors 186, 198 have been described as piezoelectric linear motors, in some embodiments, a laser system includes a motor module having other types of motors, such as stepper motors or DC motors.

What is claimed is:
1. A laser system, comprising:
a collimator configured to output a collimated laser beam;
a first support member to which the collimator is mounted;
a second support member to which the first support member is mounted;
a first linear rail along which the first support member is movable in a first direction such that the collimator, mounted to the first support member, and the collimated laser beam, outputted from the collimator, are movable in the first direction;
a second linear rail along which the second support member is movable in a second direction that is orthogonal to the first direction such that the first support member, the collimator supported thereon, and the collimated laser beam outputted from the collimator, are movable in the second direction; and
a lens positioned downstream of the collimator and configured to direct the collimated laser beam to a target location on a specimen.
2. The laser system of claim 1, further comprising an infrared laser configured to generate an infrared laser beam comprising infrared light waves with wavelengths in a range of about 700 nm to about 1 mm.
3. The laser system of claim 2, further comprising a red laser configured to generate a red laser beam comprising red light waves with wavelengths in a range of about 620 nm to about 700 nm.
4. The laser system of claim 3, further comprising a set of optical components configured to combine the infrared laser beam and the red laser beam into one laser beam.

5. The laser system of claim 4, wherein the collimator is configured to receive the one laser beam as a divergent laser beam and to output the divergent laser beam as the collimated laser beam.

6. The laser system of claim 5, further comprising a control module configured to activate the infrared laser such that the collimated laser beam, carrying the infrared light waves, can produce a hole in a structure of the specimen at the target location.

7. The laser system of claim 6, wherein the specimen is an embryo, and wherein the structure of the specimen is a zona pellucida of the embryo.

8. The laser system of claim 6, further comprising system software by which a user can select the target location and instruct the control module to activate the infrared laser.

9. The laser system of claim 4, further comprising a fiber optic cable configured to carry the one laser beam to the collimator.

10. The laser system of claim 1, wherein the first linear rail defines a rectangular recess.

11. The laser system of claim 10, wherein the first support member defines a corresponding rectangular recess.

12. The laser system of claim 11, further comprising a ball bearing configured to slide simultaneously within the rectangular recess of the first linear rail and within the corresponding rectangular recess of the first support member to movably couple the support member to the linear rail.

13. The laser system of claim 1, further comprising a motor configured to move the first support member along the first linear rail.

14. The laser system of claim 1, wherein the lens is configured to refract the collimated laser beam towards a central axis of the lens when the collimated laser beam is outputted from the collimator at a position spaced apart from the central axis of the lens.

15. The laser system of claim 1, further comprising a microscope objective positioned downstream of the lens and configured to capture the collimated laser beam and to focus infrared light waves and visible light waves within the collimated laser beam at a same plane within the specimen.

16. The laser system of claim 1, further comprising a dichroic mirror configured to reflect infrared light waves within the collimated laser beam, to reflect a first portion of visible light waves within the collimated laser beam, and to transmit a second portion of the visible light waves within the collimated laser beam.

17. The laser system of claim 16, wherein the dichroic mirror is positioned in a fixed orientation with respect to the lens.

18. The laser system of claim 1, further comprising a filter configured to block transmission of infrared light waves within the collimated laser beam.

19. A laser system, comprising:
a collimator configured to output a collimated laser beam;
a support member to which the collimator is mounted, the support member defining a first rectangular recess;
a linear rail along which the support member is movable in a first direction such that the collimator, mounted to the support member, and the collimated laser beam, outputted from the collimator, are movable in the first direction, the linear rail defining a second rectangular recess corresponding to the first rectangular recess of the support member;
a ball bearing configured to slide simultaneously within the first and second rectangular recesses to movably couple the support member to the linear rail; and
a lens positioned downstream of the collimator and configured to direct the collimated laser beam to a target location on a specimen.

* * * * *